United States Patent [19]
Dahl et al.

[11] Patent Number: 5,203,348
[45] Date of Patent: Apr. 20, 1993

[54] SUBCUTANEOUS DEFIBRILLATION ELECTRODES

[75] Inventors: Roger W. Dahl, Andover; David K. Swanson; Stephen J. Hahn, both of Roseville; Douglas J. Lang, Arden Hills; John E. Heil, St. Paul, all of Minn.

[73] Assignee: Cardiac Pacemakers, Inc., St. Paul, Minn.

[21] Appl. No.: 533,886

[22] Filed: Jun. 6, 1990

[51] Int. Cl.$^5$ .............................................. A61N 1/05
[52] U.S. Cl. .............................. 128/784; 128/419 D; 128/799; 128/642
[58] Field of Search .......... 128/784, 783, 786, 419 D, 128/419 P, 799, 798, 642

[56] References Cited

U.S. PATENT DOCUMENTS

| | | | |
|---|---|---|---|
| 3,333,045 | 7/1967 | Fisher et al. | 128/784 |
| 3,543,761 | 12/1970 | Bradley | 128/784 |
| 3,572,344 | 3/1971 | Bolduc | 128/419 P |
| 3,760,812 | 9/1973 | Timm et al. | |
| 3,866,615 | 2/1975 | Hewson | 128/784 |
| 4,006,748 | 2/1977 | Schulman | 128/419 P |
| 4,010,755 | 3/1977 | Preston | 128/419 P |
| 4,026,303 | 5/1977 | Babotai | 128/419 P |
| 4,030,509 | 6/1977 | Heilman et al. | 128/784 |
| 4,270,549 | 6/1981 | Heilman | 128/784 |
| 4,291,707 | 9/1981 | Heilman et al. | 128/419 D |

(List continued on next page.)

FOREIGN PATENT DOCUMENTS

| | | | |
|---|---|---|---|
| 0529945 | 7/1954 | Belgium | 128/799 |
| 0211166 | 2/1987 | European Pat. Off. | 128/784 |
| 0756582 | 6/1931 | France | 128/798 |

OTHER PUBLICATIONS

*Cardiac Pacing and Elecrophysiology Proceedings of VIII World Synp. on C. P. and Elephys.*, Jerusalem, Israel, Jun. 7–11, 1987, Belhassen, Feldman and Copperman (Eds.), "Electrode System for Closed Chest Ventricular Defibrillation", )Obel et al.), pp. 465–472.

"Nonthoracotomy Internal Defibrillation in Dogs: Threshold Reduction Using a Subcutaneous Chest Wall Electrode With a Transvenous Catheter Electrode" Jule Wetherbee et al., *JACC*, vol. 10, No. 2, Aug., 1987:406–411.

"Transvenous and Subcutaneous Electrode System for an Implantable Defibrillator Improved on Large Pigs", (Cansell et al.), *Pace*, vol. 11, Nov., 1988, pp. 2008–2014.

NASPE Abstract, entitled "Substitution of a Defibrillation Catheter Electrode(s) for a Subcutaneous Patch May Improve Efficacy of a Non-Thoracotomy Lead System", (Accorti et al.), *Pace*, vol. 13, Apr., 1990, p. 535.

*Primary Examiner*—Kyle L. Howell
*Assistant Examiner*—Kennedy J. Schaetzle
*Attorney, Agent, or Firm*—Haugen and Nikolai

[57] ABSTRACT

Implantable electrodes for defibrillation are formed of pluralities of electrode segments. Each of the segments is relatively long and narrow. The electrode segments can be parallel and spaced apart from one another a distance at least ten times the nominal width, with one end of each segment mounted to a transverse distal portion of an electrically conductive lead coupling the electrode to a defibrillation pulse generator. Alternatively, segments can branch or radiate outwardly from a common junction. In yet another arrangement, electrode segments are portions of a single conductive path at the distal end of a lead from a pulse generator, arranged in either a spiral configuration or a serpentine configuration which can align electrode segments side by side, parallel and spaced apart. The electrode segments can be formed of composite conductors in the form of titanium ribbons or wires with a sputtered outer layer of platinum, or a silver core in a stainless steel tube, with a platinum layer formed onto the tube. The electrodes are highly compliant yet can provide large effective areas for defibrillation, enabling a transthoracic pulsing arrangement of two electrodes on opposite sides of the heart, implanted subcutaneously outside of the thoracic region.

17 Claims, 5 Drawing Sheets

U.S. PATENT DOCUMENTS

| | | | |
|---|---|---|---|
| 4,314,095 | 2/1982 | Moore et al. | 128/642 |
| 4,341,221 | 7/1982 | Testerman | 128/642 |
| 4,522,212 | 6/1985 | Gelinas et al. | 128/784 |
| 4,567,900 | 2/1986 | Moore | 128/784 |
| 4,603,705 | 8/1986 | Speicher et al. | 128/786 |
| 4,641,656 | 2/1987 | Smits | 128/784 |
| 4,677,989 | 7/1987 | Robblee | 128/419 P |
| 4,760,852 | 8/1988 | Lekholm | 128/784 |
| 4,774,952 | 10/1988 | Smits | 128/419 D |
| 4,817,634 | 4/1989 | Holleman | 128/784 |
| 4,860,769 | 8/1989 | Fogarty et al. | 128/786 |
| 4,938,231 | 7/1990 | Milijasevic et al. | 128/784 |
| 4,998,975 | 3/1991 | Cohen et al. | 128/784 |
| 5,005,587 | 4/1991 | Scott | 128/786 |
| 5,016,645 | 5/1991 | Williams et al. | 128/784 |
| 5,042,463 | 8/1991 | Lekholm | 128/784 |
| 5,044,374 | 9/1991 | Lindemans et al. | 128/784 |

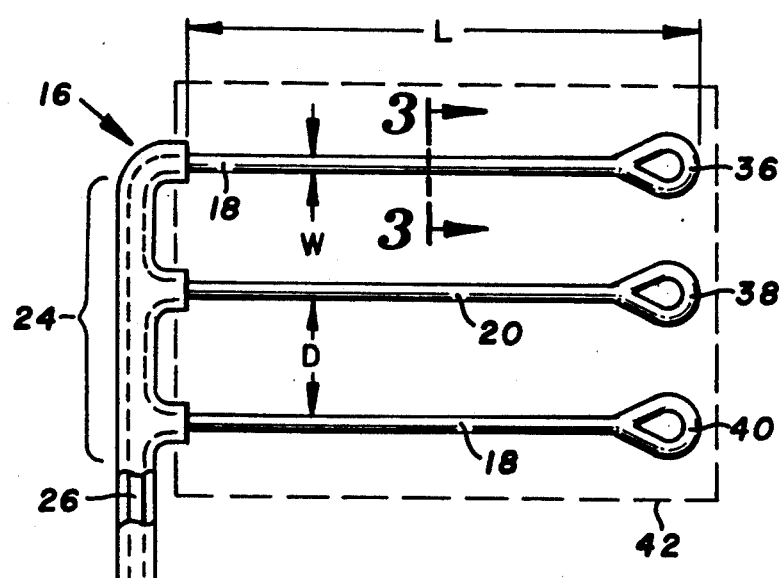
FIG. 1
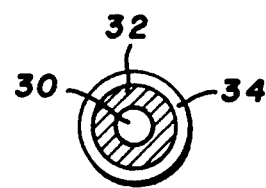
FIG. 2
FIG. 3
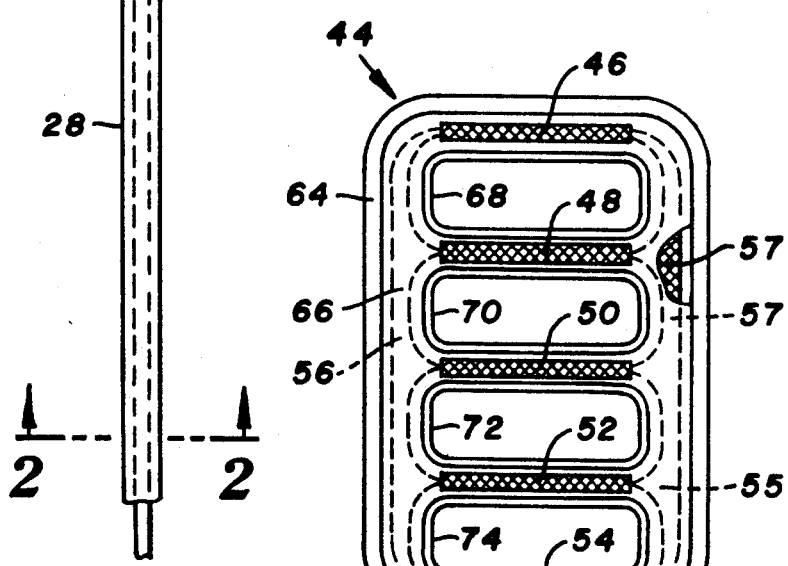
FIG. 4
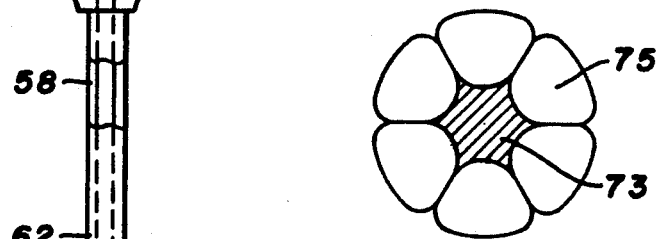
FIG. 5

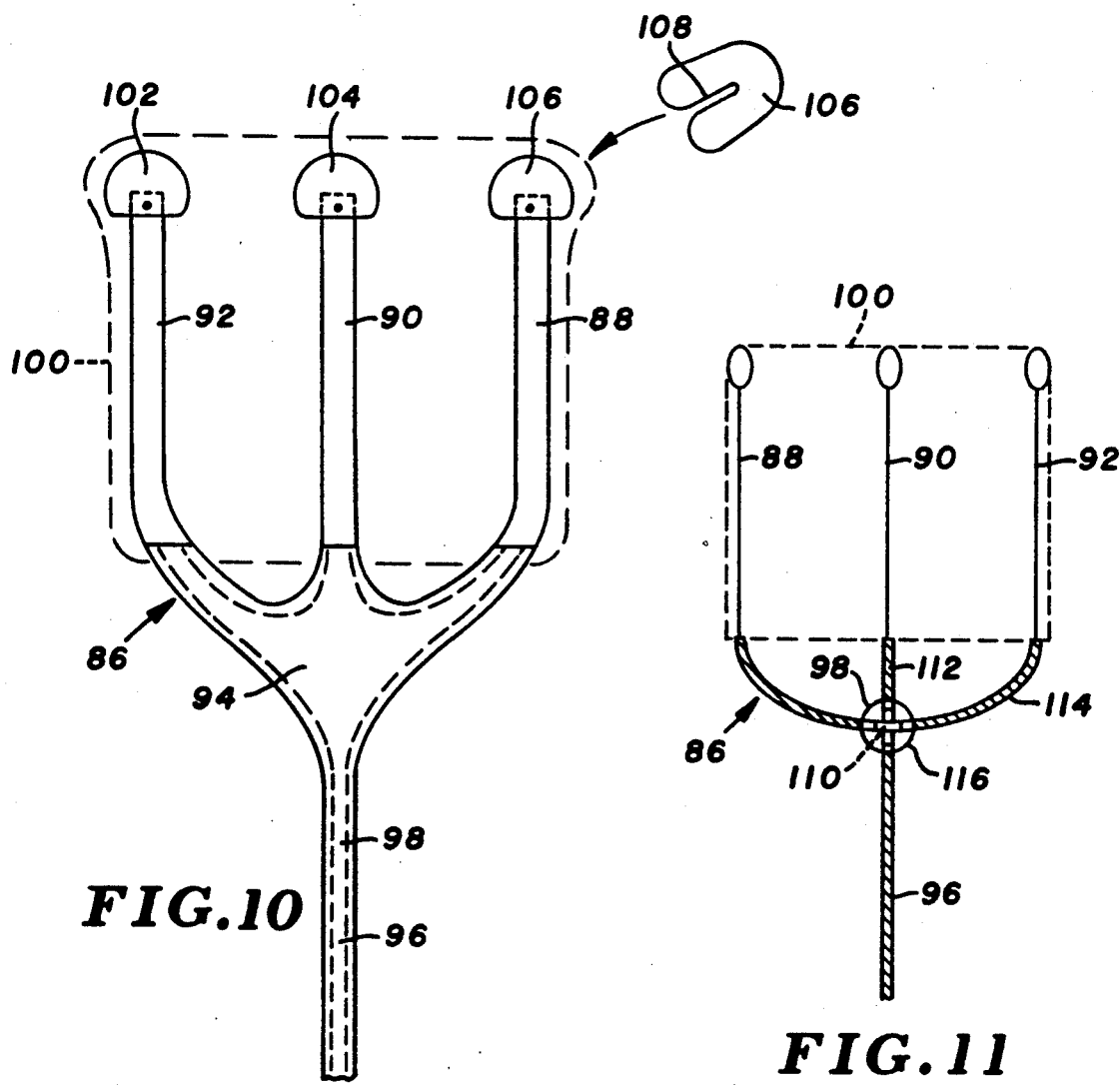

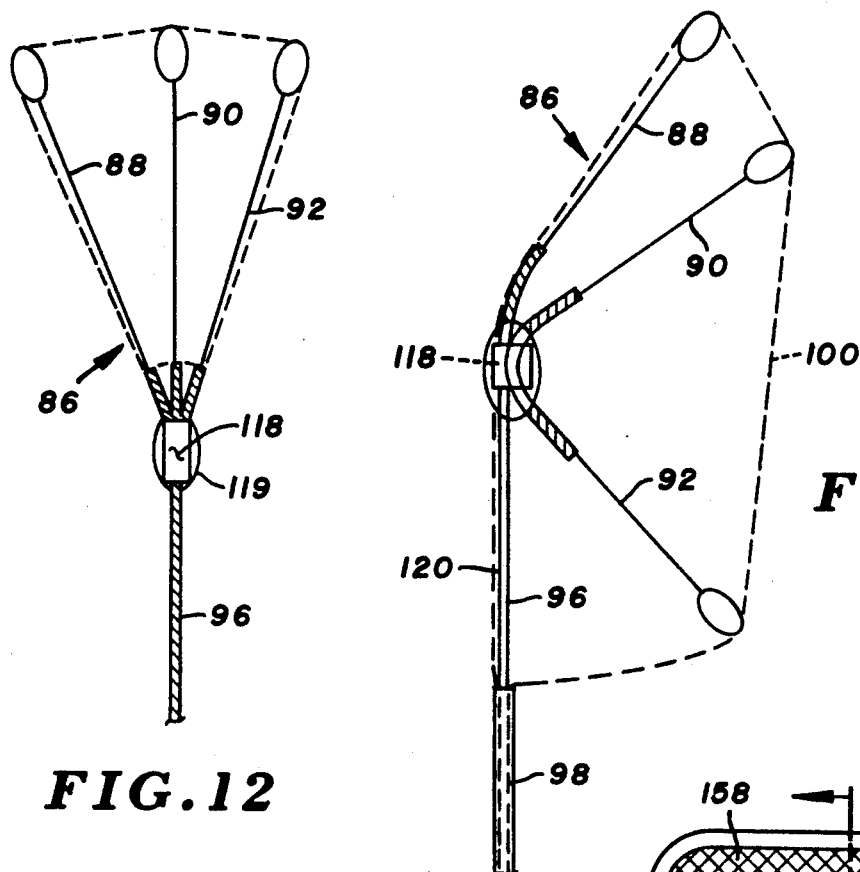
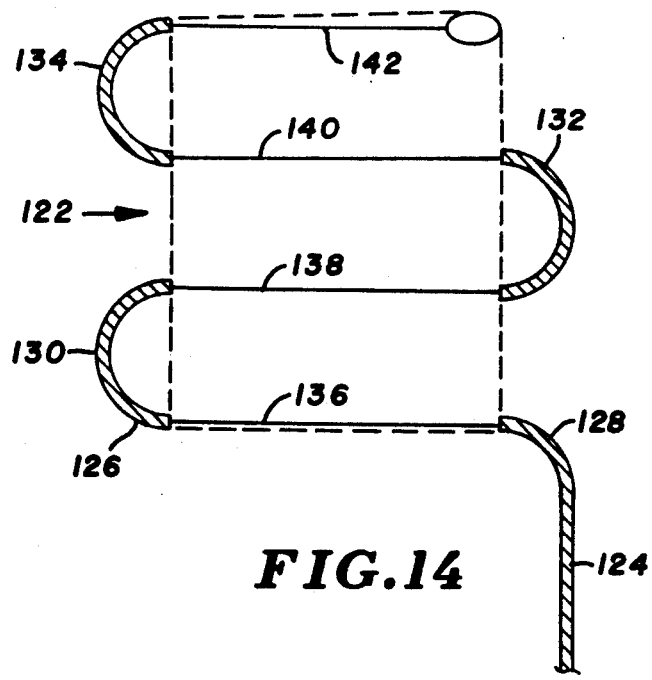
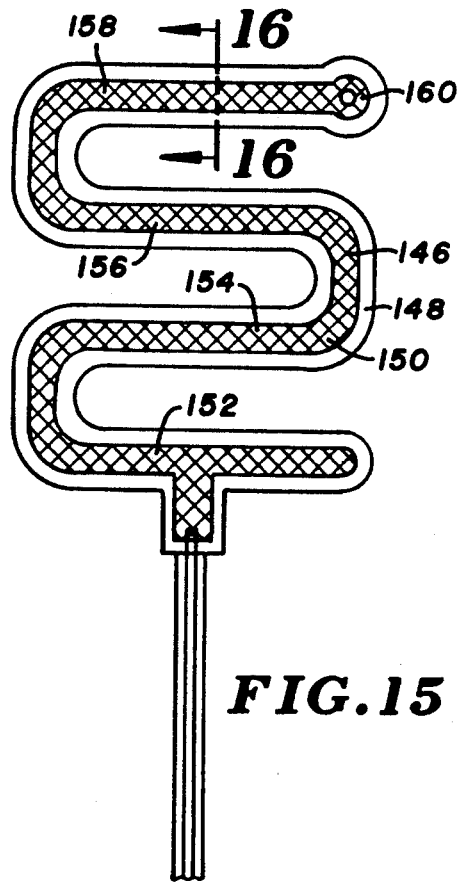

SUBCUTANEOUS DEFIBRILLATION ELECTRODES

BACKGROUND OF THE INVENTION

The present invention relates to field of electrical defibrillation, including cardioversion, and more particularly to the structure for an electrode used in implantable defibrillation systems. The term "defibrillation", as used herein, includes cardioversion which is another technique involving relatively high energy delivery, as compared to pacing, as well as other aspects of defibrillation therapy such as the monitoring of cardiac electrical activity (sensing) when not delivering high energy impulses.

Defibrillation is a technique employed to counter arrhythmic heart conditions including some tachycardias, flutter and fibrillation in the atria and/or ventricles. Typically, electrodes are employed to stimulate the heart with electrical impulses or shocks, of a magnitude substantially greater than pulses used in cardiac pacing. One defibrillation approach involves placing electrically conductive paddle electrodes against the chest of the patient. During cardiac surgery, such paddles can be placed directly against the heart to apply the necessary electrical energy.

More recent defibrillation systems include body implantable electrodes. Such electrodes can be in the form of patches applied directly to epicardial tissue, or at the distal end regions of intravascular catheters, inserted into a selected cardiac chamber. U.S. Pat. No. 4,603,705 (Speicher et al), for example, discloses an intravascular catheter with multiple electrodes, employed either alone or in combination with an epicardial patch electrode. Compliant epicardial defibrillator electrodes are disclosed in U.S. Pat. No. 4,567,900 (Moore).

Epicardial electrodes are considered the most efficient, in the sense that less energy is required for defibrillation as compared to either chest contact paddles or intravascular catheter electrodes. However epicardial electrode implantation is highly invasive, major surgery, since it is necessary to enter the chest cavity, which typically involves spreading of adjacent ribs or splitting of the sternum. This procedure presents a risk of infection. Further, implantation and attachment place physical constraints upon the nature of electrode. These electrodes must be either quite small, or extremely compliant and resistant to fatigue, as they maintain conformal fit to the contracting heart.

Generally, larger defibrillation electrodes are considered more desirable, since they reduce the impedance at or near the electrode. Sensing artifacts also are reduced for larger electrodes. However, larger electrodes are difficult to attach to the epicardium, as they must conform to the heart during the contractions associated with normal cardiac activity. Subcutaneous electrodes are more easily implanted, at less risk to the patient. In a defibrillation electrode or any other implanted device, however, increasing the size generally increases discomfort and surgical risk to the patient.

Increasing the size of a defibrillation electrode affects its electrical performance. Conventional electrodes are subject to "edge effects" arising from the non-uniform distribution of electrical energy when the electrode receives the pulse. In particular, current densities are greater at the edges of the electrode than at interior regions of the electrode. An attempt to counter the edge effect is disclosed in U.S. Pat. No. 4,291,707 (Heilman et al). A series of circular openings, through an insulative layer framing a conductive screen, are said to substantially eliminate the edge effect by the additional exposure of the screen. Another problem encountered in larger electrodes is the resistance across the length (largest linear dimension) of the electrode, leading to unwanted voltage gradients across the electrode which can degrade electrode performance.

Therefore, it is an object of the present invention to provide an implantable defibrillation electrode with a large effective surface area to lower the impedance at or near the electrode, without causing undue patient discomfort.

Another object is to provide a defibrillation electrode that has a large effective area, yet is easier to implant and readily conforms to the contours of its implant location.

A further object is to provide a defibrillation electrode structure enabling a relatively large size while reducing the non-uniform field distribution associated with conventional electrodes.

Yet another object is to provide defibrillation electrodes of sufficient size and effectiveness to enable transthoracic delivery of defibrillation pulses, with an implanted system.

SUMMARY OF THE INVENTION

To achieve these and other objects, there is provided a body implantable tissue stimulating electrode. The electrode includes a plurality of flexible, electrically conductive electrode segments having a nominal width and a length at least five times the nominal width. A means is provided for mechanically coupling the electrode segments with respect to one another whereby each of the segments, over the majority of its length, is spaced apart from each one of the other segments by a distance of at least 1.5 cm. A means is provided for electrically coupling the electrode segments for substantially simultaneous reception of the tissue stimulating electrical pulses from a pulse generating means. Consequently the electrode segments, when receiving the tissue stimulating pulses, cooperate to define an effective electrode area incorporating the electrode segments and having a width of at least 1.5 cm.

In one preferred configuration, the electrode segments are linear and in parallel spaced apart relation, all extending in a longitudinal direction. The mechanical and electrical coupling means can be a transversely extended distal portion of an elongate, electrically conductive lead. The lead is connected to each of the respective first end portions of the electrode segments along its distal region, and connected at its proximal end to a pulse generating means. Preferably an electrically insulative layer covers the lead, leaving the electrode segments exposed, to define a substantially rectangular "phantom" area or effective electrode area.

Alternatively, the electrode segments can radiate outwardly from a common junction, typically at the distal end of the lead or conductive coupling wire from the pulse generating means. While the coupling wire is covered with an insulative material over the majority of its length, a distal end portion of the coupling wire can be left exposed, to provide one of the electrode segments.

Yet another approach involves a single electrically conductive wire or path, with portions of the path providing the spaced apart segments. As an example, the path can be arranged in a serpentine configuration in which segments are parallel to and aligned with one another, side by side. Alternatively, the conductive path is formed as a spiral. In either event, adjacent segments are spaced apart from one another a distance substantially greater than their width, preferably by an order of magnitude or more.

In a preferred example, elongate electrode segments about 30 cm long and with a nominal width of 0.5 mm extend longitudinally, aligned with one another and spaced apart from one another by about 3 cm. One end of each electrode segment is mounted to the distal end portion of a conductive lead to a pulse generator. At the opposite, free end of each segment is an enlargement such as a loop or flared end, formed to minimize local high current densities due to the previously described edge effects. The combination of a large phantom area with multiple conductive segments reduces non-uniform current distributions.

The best results are achieved with highly conductive electrode segments. Accordingly, the segments are preferably formed of low resistance composite conductors including drawn braised strands (DBS), drawn filled tubes (DFT) and the like, coated with platinum or another metal from the platinum group, e.g. iridium, ruthenium or palladium, or alternatively with an alloy of one of these metals. The strands can be formed of titanium or platinum. A suitable filled tubular conductor is composed of a silver core within a stainless steel tube. The electrode segments can be formed of single wires, pluralities of wires in a braided or twisted configuration, helically wound coils, or a woven mesh or screen. In some embodiments, particularly those employing the woven screen, it is further desirable to include an insulative backing to more positively position the electrode segments with respect to one another.

It has been found that highly conductive electrode segments reduce any voltage gradient across the electrode, with the separate segments simultaneously receiving a defibrillation or other stimulation pulse. The separate segments thus cooperate to act as a single "patch" electrode, having an effective surface area equal to that of a rectangle or other polygon containing all of the segments. As an example, an electrode formed as a row of five parallel electrode segments spaced apart from one another by 3 cm, each segment being 10 cm long, would have a rectangular phantom or effective area slightly larger than 120 (twelve times ten) square cm. Yet, as compared to a continuous rectangular patch electrode measuring ten by twelve cm, the branched segment electrode in accordance with the present invention is easier to implant, reduces the high current density regions, and more easily conforms to the thorax or other surface to which it is attached. In fact, branched arrangements of segments can provide effective defibrillation electrode areas in the range of from 100 to 200 square cm, while enabling easy implantation.

Thus, in accordance with the present invention there is disclosed a process for applying defibrillation pulses to a human heart, including the following steps:

(a) implanting a first compliant electrode in a patient, proximate the pleural cavity and the rib cage, and on a first side of the thoracic region of the body;

(b) implanting a second compliant electrode in the body, proximate the pleural cavity, and the rib cage, and on a second side of the thoracic region opposite the first side, with at least a portion of the heart between the first and second electrodes;

(c) implanting a defibrillation pulse generator; and (d) electrically coupling the first and second electrodes to a defibrillation pulse generator and providing defibrillation pulses from the pulse generator across the first and second electrodes.

If desired, one or more electrodes implanted proximate the pleural cavity and rib cage can be used in combination with one or more coil electrodes mounted on an intravascular catheter, preferably positioned in the right atrium and the right ventricle of the heart, with the distal end of the catheter near the apex of the right ventricle.

As compared to the entry into the chest cavity normally associated with implanting epicardial electrodes, transthoracic placement of subcutaneous electrodes as outlined above is substantially less invasive, preserves the integrity of the rib cage and the pleural cavity, and reduces risk of infection.

Nonetheless, other implant locations, including direct attachment to epicardial tissue, can be employed in accordance with the present invention, to achieve relatively large effective electrode areas while maintaining patient comfort with substantially more uniform distribution current density.

IN THE DRAWINGS

For a further understanding of the above and other features and advantages, reference is made to the detailed description and to the drawings, in which:

FIG. 1 is a top plan view of a defibrillation electrode constructed in accordance with the present invention;

FIG. 2 is a sectional view taken along the line 2—2 in FIG. 1;

FIG. 3 is a sectional view taken along the line 3—3 in FIG. 1;

FIG. 4 is a top plan view of an alternative embodiment electrode constructed in accordance with the present invention;

FIGS. 5-9 illustrate alternative constructions for electrode segments of the electrodes;

FIG. 10 is plan view of another alternative embodiment electrode constructed in accordance with the present invention:

FIGS. 11-13 illustrate further alternative configurations of the electrode of FIG. 9;

FIG. 14 is a top plan view of another alternative embodiment electrode;

FIGS. 15, 16 and 17 illustrate a further embodiment electrode;

DETAILED DESCRIPTION OF THE PREFERRED EMBODIMENTS

Figure 16:

Turning now to the drawings, there is shown in FIG. 1 a defibrillation electrode 16 including three parallel and spaced apart electrode segments 18, 20 and 22. Each of the segments has a length (L in the figure) substantially longer than its width (W), e.g. 30 cm long with a nominal width preferably about 0.5 mm. Generally, the width should be within the range of from 0.25-5 mm. Adjacent segments are spaced apart a distance (D) substantially greater than the nominal width, e.g. 3 cm. This center-to-center spacing should be at least 1.5 cm, and preferably does not exceed 30 cm.

Electrode segments 18, 20 and 22 are fixed at respective first ends to a distal end portion 24 of an electrically conductive lead 26. The lead conducts electrical pulses to the electrode segments from a pulse generator (not shown) coupled to the proximal end of the lead. Lead 26 at the distal end structurally supports the longitudinally extended electrode segments in the transversely spaced apart configuration shown.

The electrically conductive portion of lead 26 is surrounded by an electrically insulative cover or sheath 28, preferably constructed of a body compatible polymer, e.g. a medical grade silicone rubber or polyurethane. As seen in FIG. 2, the lead includes a composite conductor formed of a core 30 of silver surrounded by a tube 32 of stainless steel. This type of composite conductor is known as drawned field tube (DFT) of MP35N (brand-name) alloy available from FWM Research Products of Fort Wayne, Ind. Further, a coating 34 of platinum is applied over the stainless steel, preferably by sputtering or other deposition process. While preferably platinum, coating 34 also can consist of another metal from the platinum group (e.g. iridium, ruthenium and palladium) or an alloy of these metals. Insulative sheath 28 is contiguous with and surrounds the platinum layer.

As seen in FIG. 3, the construction of electrode segment 22 (and likewise segments 18 and 20) over substantially all of its length is substantially similar to the construction of the conductive portion of lead 26. Thus the segments also are highly electrically conductive. Platinum coating 34 provides a further advantage for the segments, which are not covered by the insulative sheath. In particular, the platinum coating when applied by vapor deposition provides a microtexture which substantially increases the reactive surface area of the electrode segments, to reduce near field impedance of the electrode (the term "near field" impedance refers to the voltage losses associated with the electrode due to chemical and field effects). For a further discussion of this feature, reference is made to U.S. Pat. No. 5,074,313 assigned to the assignee of the present application. The reduced interface impedance increases the ratio of bulk impedance to the total system impedance as measured between the stimulating electrode and the indifferent or signal return electrode. Thus, more of the voltage drop occurs across tissue, where it is useful for causing the desired stimulation, with proportionately less of the voltage drop occurring at the electrodes where it is non-productive. This enables a reduction in overall potential or pulse duration, in either event reducing the required energy for defibrillation.

Given adequate separation between segments 20, 22 and 24, the current distribution is made more uniform. To further counter any current density differentials due to edge effects at the ends of segments 20, 22 and 24, loops 36, 38 and 40 are formed at these ends, respectively. Alternatively, the ends can be flared or otherwise enlarged, and remain substantially free of undesirable concentrations of high current. Such enlargements also facilitate implant, as they tend to positionally fix the electrode segments.

Because the electrode segments are electrically common, the electrodes receive and transmit defibrillation pulses simultaneously. The electrode segments are sufficiently near one another to function in concert, providing an effective area or phantom area incorporating the segments, as indicated in broken lines at 42. In other words, electrode segments 20, 22 and 24 define a generally rectangular effective area, with substantially greater compliance to contours and movements of body tissue, as compared to a continuous patch electrode. In addition, the spacing between electrodes performs an important electrical function by producing a substantially more uniform current distribution than that of a continuous patch electrode. Patch electrodes are known to have regions of very high current density around their outside edges, and regions of low current density at their centers. By using a segmented electrode, with segments properly spaced apart from one another, much higher currents can be delivered to the central region of the effective or phantom area because current is able to flow between adjacent segments. This results in a more uniform electrical field across the heart.

FIG. 4 illustrates an alternative embodiment defibrillation electrode 44 including five elongate electrode segments 46, 48, 50, 52 and 54, each with a preferred width and substantially greater preferred length as described in connection with electrode 16. Each of electrode segments 46–54 is part of a wire mesh pattern 55 and extends longitudinally. Transversely extended end portions 56 and 57 of the pattern couple the segments to a lead 58. An insulative sheath 62 surrounds lead 58 from electrode 44 to the proximal end of the lead. An electrically insulative backing 64 supports mesh pattern 55. The mesh pattern is covered by an insulative layer 66. Slots 68, 70, 72 and 74 are formed in backing 64 and layer 66 between adjacent electrode segments.

FIG. 5 illustrates an alternative form of composite conductor known as DBS (drawned braised strands), available from FWM Research Products, Fort Wayne, Ind. As shown, a silver core 73 is surrounded by six stainless steel wires 75. The structure is heated and drawn to braise all wires together. The results is a solid, continuous composite conductor composed of a silver core and a stainless steel outer shell or tube.

FIG. 6 illustrates an alternative construction for the electrode segments of either electrode 16 or electrode 44, involving a plurality of composite conductors 76 in a twisted configuration. Each of the conductors can include a silver core within a stainless steel tube coated with platinum as previously described. Alternative composite conductors for single and multiple wire arrangements include platinum or titanium ribbon or wire, clad with platinum. The twisted construction enhances flexibility and resistance to fatigue in the electrode segments. Other alternatives include braided or knitted wires.

FIG. 7 shows another alternative construction for the electrode segments, in the form of a woven mesh or screen 78 on an electrically insulative backing 80. This type of electrode segment construction is particularly well suited for epicardial positioning, e.g. with electrode 44 in FIG. 4.

Another alternative segment construction, shown in FIGS. 8 and 9, involves a flexible, electrically insulative cylindrical core 82 of polyurethane, medical grade silicone rubber, or other suitable body compatible material. Core 82 is surrounded by an electrically conductive coil winding 84, preferably a wire or composite cable such as illustrated in FIG. 2. The helically wound coil conductor provides the greatest flexibility and fatigue resistance of any of the arrangements discussed, and for this reason is preferred in the case of direct epicardial attachment, or any other implant location in which the lead segments are subject to continued or repeated muscular contraction or other abrupt tissue movements. A disadvantage, relative to other embodiments, is that a helical coil electrode segment, as compared to other segments of equal length, involves a substantially longer conductive path with less tensile strength.

All of the alternative constructions provide electrode segments which are highly compliant, first in the sense that they readily adjust to the contours of body tissue at the implant site when they are implanted, and secondly over the long term, in continually conforming to the tissue during muscular contractions and other tissue movement.

FIG. 10 illustrates a further embodiment defibrillation electrode 86 including electrode segments 88, 90 and 92 formed as branches, radiating or extended outwardly from a common junction and stress relief area 94. Junction 94 is positioned at the distal tip region of a lead 96 to a pulse generator (not shown), and includes a conductive portion surrounded by an insulative sheath 98. The conductive region of the lead and the electrode segments can be constructed as previously described.

The stress relief portion of the electrode is electrically insulative and covers portions of the segments, leaving exposed portions of the segments spaced apart from one another and defining an effective or phantom area 100 shown by the broken line. As before, segments 88-92 have a nominal width preferably about 0.5 mm, and are longer than they are wide, for example by at least a factor of five. At the free ends of the segments are respective masses or bodies 102, 104 and 106. The bodies are constructed of an electrically conductive, plastically deformable material such as platinum or gold and, as seen in FIG. 10, include slots 108 slightly wider than the thickness of segments 88-92. Each body is applied to the free end of its respective electrode segment by inserting the free end within the respective slot and pinching the body to frictionally secure the body to the electrode segment. Bodies 102-106 thus provide enlargements at the free ends of the segments to reduce the chance for high current densities at the free ends, and provide a means of fixation of the free ends.

FIGS. 11-13 schematically illustrate alternative configurations for electrode 86. More particularly, FIG. 11 illustrates a clamp 110 for electrically and mechanically coupling two intersecting cables 112 and 114. Cable 112 is part of lead 96, with a distal portion of the lead providing center segment 90. Electrode segments 88 and 92 are opposite portions of cable 114. An extension 116 of electrically insulative sheath 98 covers clamp 110 and portions of cables 112 and 114, leaving the segments exposed.

In FIG. 12, segments 88, 90 and 92 extend radially from a crimping member 118 at the distal end of lead 96. Alternatively, segment 90 is the distal end of the lead, in which case the remainder of the lead, crimping member 118 and portions of the electrode segments are provided with an insulative covering 119.

In FIG. 13, crimping member 118 secures electrode segments 88, 90 and 92 to the distal section 120 of lead 96. Insulative sheath 98 leaves distal section 120 exposed, so that it functions as a fourth electrode segment.

FIG. 14 shows a further embodiment defibrillation electrode 122 including a lead 124 having a distal end 126 formed in a curved, serpentine configuration. An insulative sheath 128 covers the lead and leaves the distal region exposed. Further insulation covers curved portions of the electrode at 130, 132 and 134, thus to define four parallel segments or length-portions 136, 138, 140 and 142 aligned with one another and side by side.

Figure 17:
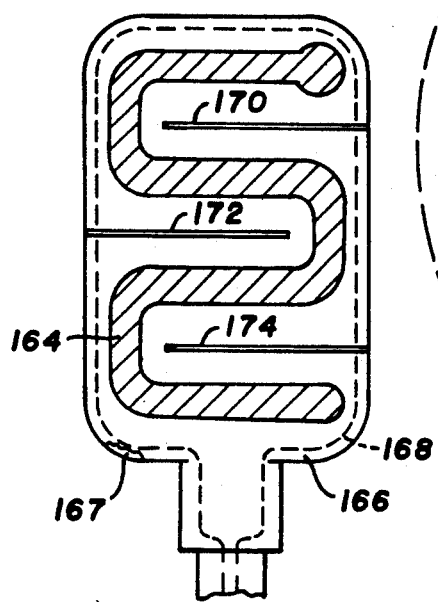

FIGS. 15, 16 and 17 disclose alternative serpentine electrode configurations including an electrode 144 with a wire mesh or screen 146 on an electrically insulative backing 148. FIGS. 15 and 16 illustrate a conductive path 150 including parallel electrode segments 152, 154, 156 and 158. The distal end of segment 158 is enlarged at 160 to counteract edge effect current densities.

In FIG. 17, an electrode 162 includes a serpentine conductive path 164 formed between a pair of generally rectangular electrically insulative layers 166 and 167. A serpentine opening in layer 166 exposes part of a wire mesh layer 168. Slits in the patches at 170, 172 and 174 allow the patch to conform to the site of implant. Selected parts of the conductive path can be covered with insulation if desired, to leave just parallel segments exposed.

Figure 18:
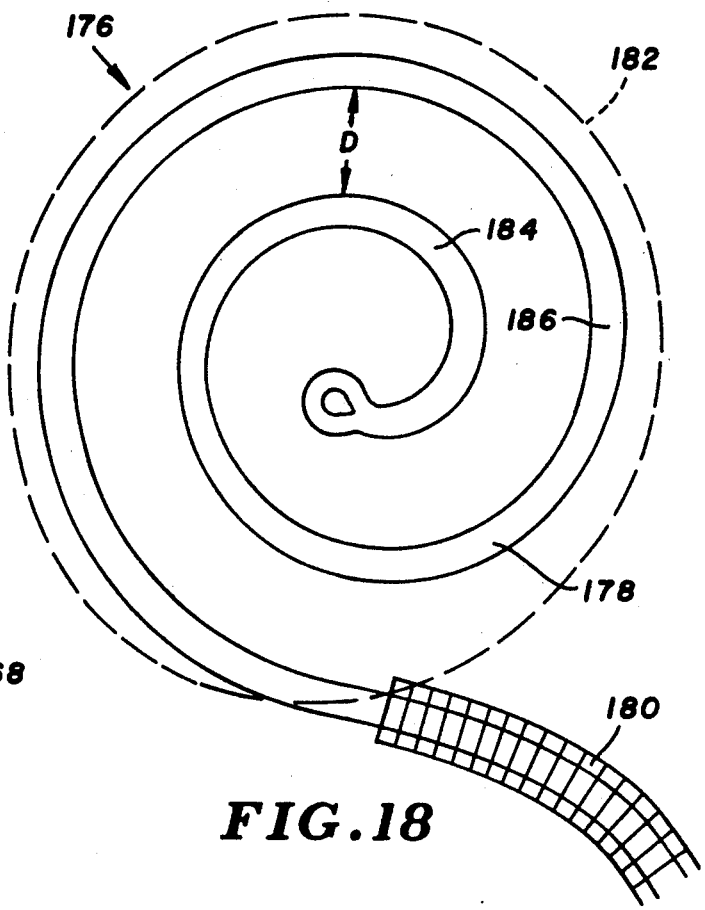
FIG. 18 is a top plan view of yet another embodiment electrode.

FIG. 18 discloses yet another embodiment defibrillation electrode 176 in which a single conductive path 178 at the distal end of a lead 180 is formed into a spiral. The path can be a coated composite cable or a wire mesh or screen as previously described, with a similar nominal width in the radial direction. The pitch of the spiral, i.e. radial spacing (D) between adjacent arcs in the spiral, is preferably about 3 cm. Thus the effective electrode area encompasses the outermost arc of the spiral, as indicated by the broken line at 182. The spiral includes at least two complete turns or length-portions as shown, with each turn forming an arcuate electrode segment to provide respective radially inward an outward segments 184 and 186.

Regardless of the particular embodiment, electrodes constructed in accordance with the present invention provide a substantially larger effective or phantom area than previously practical for implantable defibrillation electrodes. One reason for this is the spacing between adjacent electrode segments, resulting in more compliant electrodes, both in the sense of matching contours in body tissue, and "dynamically" in responding to muscular contractions and other sudden or rapid tissue movement, with virtually no risk of fatigue. Another feature permitting the large size is the highly conductive electrode segments and lead distal end or other feature electrically coupling the electrode segments. This ensures an acceptably low voltage gradient across even relatively large electrodes.

Figure 19:
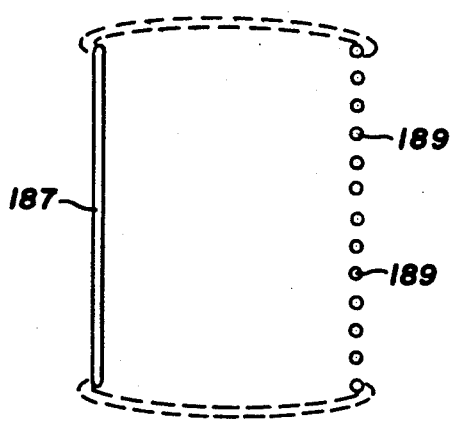
FIG. 19 is a schematic representation of the electrical field between a continuous patch electrode and an electrode having segments, but in which the segments are too close to one another.

As previously noted, a large but segmented electrode structure results in a substantially more uniform current distribution, as compared to conventional continuous patch electrodes. FIG. 19 schematically illustrates electrical current flow, in broken lines, between a continuous patch electrode 187 and an electrode composed of parallel, spaced apart wires or segments 189. Adjacent segments 189 are quite close to one another, e.g. spaced apart from one anther a distance of about 5 mm. Because of the low impedance between adjacent segments 189, there is virtually no potential difference between these segments and intervening tissue. Most of the current flow is along the end segments 189, and very little occurs near the intermediate segments or between segments. Consequently, the electrode formed of segments 189, much like electrode 187, exhibits a non-uniform current distribution, with very high current density at the outside edges and low current density along the medial region.

Figure 20:
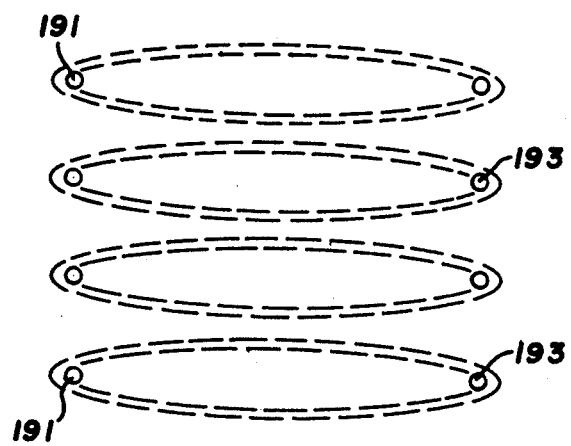
FIG. 20 is a schematic representation of the electrical field between two electrodes constructed according to the present invention.

In FIG. 20, the electrical current flow between two electrodes with respective segments 191 and 193 exhibits a substantially uniform current density across each electrode. Again the current flow is shown in broken lines, and illustrates the importance of sufficient spacing between adjacent electrode segments. More particularly, the segments of electrodes 191 and 193 are spaced apart from one another a sufficient distance for intervening tissue to provide substantial electrical impedance between adjacent electrode segments. Thus, each of segments 191 and 193, including the intermediate segments, responds to the opposite one of the electrode pair, permitting current densities, over the central regions of these electrodes, substantially equal to the current densities at their edges.

Figure 21:
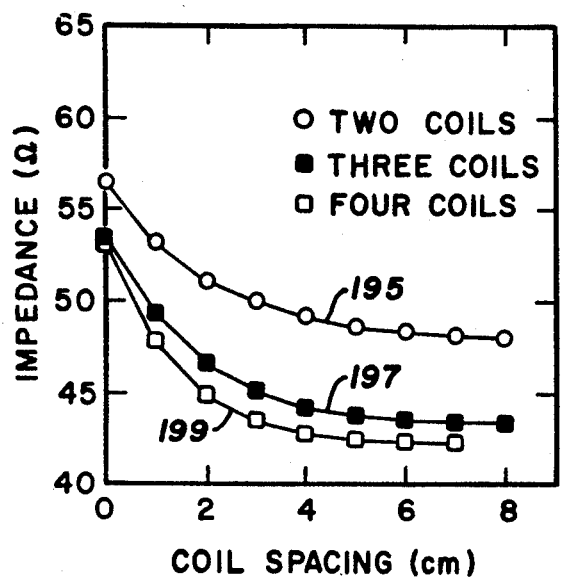
FIG. 21 is a plot of intraelectrode impedance as a function of the spacing between adjacent segments of each of the electrodes, for electrodes with from two to four segments.

FIG. 21 shows the relationship between the spacing between coils or adjacent and parallel electrode segments, and impedance, for groups of two, three and four segments as shown at 195, 197 and 199, respectively. In all cases the impedance is highest when adjacent segments are closest together. In all cases, increasing the spacing from 1 cm to the preferred 3 cm reduces impedance, and the cases show some further improvement as spacing is increased beyond 3 cm. For any selected spacing, the four segment electrode exhibits the lowest impedance, which is not surprising in view of the fact that larger electrodes generally exhibit lower impedance.

Thus, it has been found that electrode performance is substantially improved, in terms of reduced impedance as well as uniformity of the electrical field, when the spacing between adjacent segments is at least 1.5 cm. The upper limit of spacing is less strict, and subject to physical (size and patient comfort) constraints rather than electrical performance constraints. Within these limits, the optimum spacing depends upon the materials employed and the intended location of implant. Generally, however, a spacing of 3 cm between adjacent electrode segments has been found satisfactory.

Figure 22:
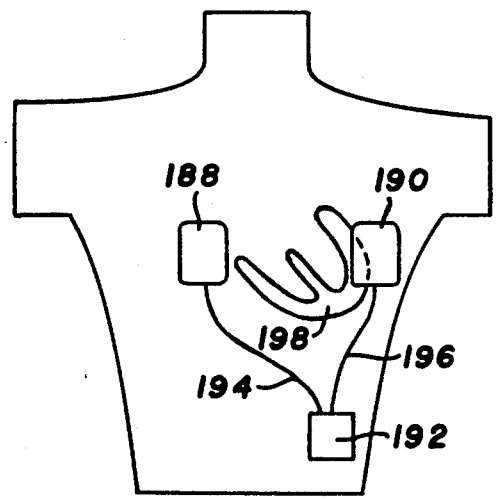
FIGS. 22, 23 and 24 diagrammatically illustrate alternative implantation approaches for defibrillation systems incorporating electrodes embodying the present invention.

FIG. 22 schematically illustrates an implanted defibrillation system including spaced apart electrodes 188 and 190, for example similar to electrode 16. The defibrillation system further includes a pulse generator 192, and leads 194 and 196 connecting the pulse generator to electrodes 188 and 190, respectively. Both of the electrodes are subcutaneous and outside of the rib cage, in the thoracic region. The electrodes are on opposite sides of the heart 198. More particularly, electrode 188 is positioned to the left of, and anterior with respect to, the heart. Electrode 190 is posterior with respect to the heart, and to the right of the heart. Such transthoracic application of defibrillation pulses requires electrodes having a large surface area, achieved in accordance with the present invention by the spaced apart electrode segments of each electrode. Pulse generator 192 is also mounted anterior and to the left of heart 198, below electrode 188. The pulse generator can incorporate circuitry for sensing cardiac electrical activity, in which case electrodes 188 and 190 are used in sensing such activity as well as delivering defibrillation pulses.

Figure 23:
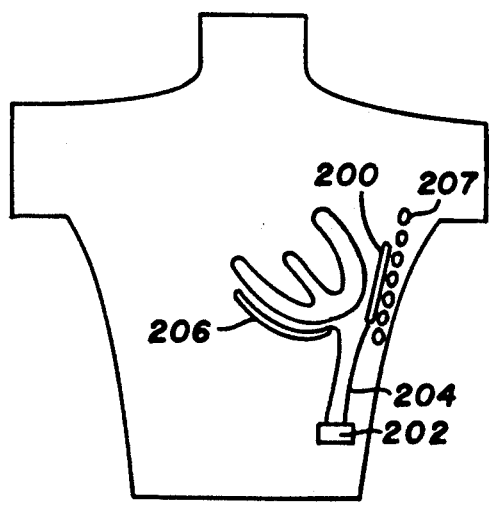

FIG. 23 discloses a defibrillation system in which an electrode 200 constructed in accordance with the present invention is coupled to a defibrillation pulse generator 202 by a lead 204. Another electrode 206, also constructed according to the present invention, is applied directly to epicardial tissue. Electrode 200 is positioned inside of rib cage 207, and can be within the pleural cavity if desired. Stimulation occurs across the heart, with electrode 200 to the left of the heart and electrode 206 at the right ventricle.

Figure 24:
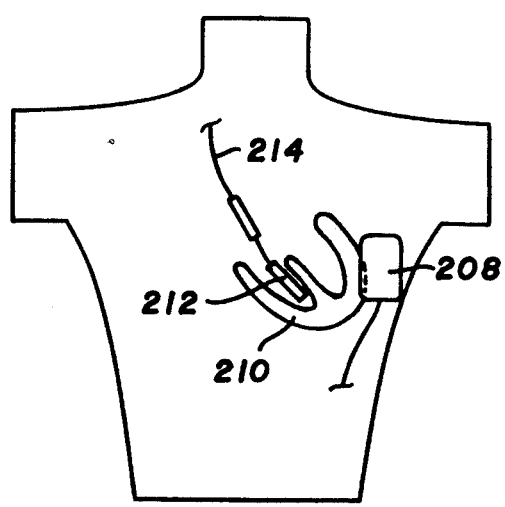

FIG. 24 shows a defibrillation electrode system including an electrode 208 positioned anterior of and to the left of the heart 210, as in FIG. 22. A second electrode 212 is provided as a coil, near the distal end of an intravascular catheter 214 in the right atrium and terminating at the apex of the right ventricle.

Regardless of the location of implant, electrodes, constructed in accordance with the present invention provide relatively large (in the range of 100–300 square cm) effective areas, yet readily conform to contours and contractions or other movement of body tissue. The narrow electrode segments are provided with end loops or other enlargements to counteract high current densities due to edge effects and to provide fixation. The present lead configurations further allow a subcutaneous implantation outside of the rib cage, with effective defibrillation energy production due to large virtual sizes based on the phantom areas incorporating the electrode segments.

What is claimed is:

1. A body implantable tissue stimulating electrode assembly, including:
   an elongate, electrically conductive lead having a proximal end region and a distal end region; and
   an electrode including a plurality of compliant, electrically conductive electrode segments, each of said segments having a nominal width of at most five millimeters and a length exceeding the nominal width, said electrode segments having respective and opposite first and second ends and being coupled to the distal end region of the lead for substantially simultaneous reception of tissue stimulating electrical pulses from a pulse generating means at the proximal end region of the lead, said electrode segments being arranged in spaced apart and side-by-side relation such that each of the electrode segments, over most of its length, is spaced apart from each one of the other electrode segments by a distance of at least 1.5 cm, each of the electrode segments being free of electrically insulative material at and along its periphery substantially over its entire length to provide an exposed reactive surface over substantially the entire length and periphery of the electrode segment, each of said electrode segments including at least one electrically conductive cable having a highly conductive metal core within in a conductive metal tube, said electrode segments when receiving the tissue stimulating pulses cooperating to define an effective electrode area incorporating all of the electrode segments.

2. The assembly of claim 1 wherein:
   said electrode segments are linear and in parallel, spaced apart relation to one another, and the length is at least five times the width.

3. The assembly of claim 2 wherein:

said electrode segments are connected at their respective first ends to the distal region of the lead, and extend in a first direction from the distal end region.

4. The assembly of claim 3 further including:

an electrically insulative layer covering the distal end region of the lead.

5. The assembly of claim 1 further including:

a layer covering the metal tube and consisting essentially of one or more of the following: platinum, iridium, ruthenium and palladium.

6. The assembly of claim 1 wherein:

each of the electrode segments includes a plurality of said electrically conductive cables wound together in a twisted configuration.

7. The assembly of claim 1 wherein:

each of the electrode segments includes at least one electrical conductor wound in a helical coil.

8. The assembly of claim 7 wherein:

each of the electrode segments further includes a flexible, electrically insulative cylindrical core, with said at least one electrical conductor being wound about the cylindrical core.

9. The assembly of claim 1 wherein:

said distal end region includes a common junction, and each of the electrode segments extends radially outwardly of the common junction.

10. The assembly of claim 9 wherein:

a single electrically conductive path forms first and second ones of the electrode segments, and a third one of the segments is joined to the midpoint of the electrically conductive path.

11. The assembly of claim 9 wherein:

the distal end region of the lead forms a first one of the electrode segments, and remaining one of the electrode segments are coupled to the first electrode segment.

12. The assembly of claim 11 further including:

an electrically insulative layer substantially covering the lead but leaving the distal end region exposed.

13. A body implantable tissue stimulating electrode assembly, including:

an elongate, electrically conductive lead having a proximal end region and a distal end region; and a substantially planar electrode formed of a compliant and electrically conductive pattern body constructed of a conductive wire mesh, a first insulative layer covering a first side of the body, a second insulative layer covering a second and opposite side of the body, and a plurality of elongate openings through at least one of said first and second insulative layers, said elongate openings being selectively positioned to expose portions of the body comprised of a plurality of electrode segments, each of the electrode segments being spaced apart from the other electrode segments by a distance of at least 1.5 cm, and wherein the length of each electrode segment is at least five times the width of the electrode segment;

said pattern body further having substantially parallel and spaced apart first and second end portions coupled to respective first and second opposite ends of the electrode segments, with at least the first end portion being coupled to the distal end portion of the lead; and said electrode segments being parallel to one another and extended in a first direction, and wherein the first end portion and the second end portion extend in a second direction substantially perpendicular to the first direction.

14. A body implantable tissue stimulating electrode assembly, including:

an elongate, electrically conductive lead having a proximal end region and a distal end region; and an electrode including a plurality of compliant, electrically conductive electrode segments, each of said segments having a nominal width and a length at least five times the nominal width, said electrode segments having respective and opposite first and second ends and being coupled to the distal end region of the lead for substantially simultaneous reception of tissue stimulating electrical pulses from a pulse generating means at the proximal end region of the lead, said electrode segments being arranged in spaced apart and side-by-side relation such that each of the electrode segments, over most of its length, is spaced apart from each one of the other electrode segments by a distance of at least 1.5 cm, each of the electrode segments being free of electrically insulative material at and along its periphery substantially over its entire length to provide an exposed reactive surface over substantially the entire length and periphery of the electrode segment, said electrode segments when receiving the tissue stimulating pulses cooperating to define an effective electrode area incorporating all of the electrode segments; said electrode segments being linear and in parallel, spaced apart relation to one another; and electrically conductive means at the respective second ends of the electrode segments for reducing current density.

15. The assembly of claim 14 wherein:

said means at the respective second ends include respective electrically conductive loops.

16. The assembly of claim 14 wherein:

said means at the respective second ends include respective electrically conductive tab enlargements.

17. The assembly of claim 14 wherein:

said means at the respective second ends include respective electrically conductive bodies, each secured to its respective one of the second ends.

* * * * *